United States Patent
Karmali

(10) Patent No.: US 9,089,570 B2
(45) Date of Patent: *Jul. 28, 2015

(54) COMPOSITIONS FOR TREATING CANCERS HAVING ACQUIRED RESITANCE TO PRIOR CHEMOTHERAPEUTIC AND TARGETED DRUGS USING CARBOXYAMIDOTRIAZOLE OROTATE

(71) Applicant: Rashida A Karmali, Brooklyn, NY (US)

(72) Inventor: Rashida A Karmali, Brooklyn, NY (US)

(73) Assignee: TACTICAL THERAPEUTICS INC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/986,103

(22) Filed: Apr. 1, 2013

(65) Prior Publication Data

US 2014/0294806 A1   Oct. 2, 2014

(51) Int. Cl.
- *A61K 31/41* (2006.01)
- *A61K 31/513* (2006.01)
- *A61K 45/06* (2006.01)
- *A61K 31/4192* (2006.01)

(52) U.S. Cl.
CPC .............. *A61K 31/513* (2013.01); *A61K 45/06* (2013.01); *A61K 31/4192* (2013.01)

(58) Field of Classification Search
CPC .................................................. A61K 31/4192
USPC ......................................................... 514/359
See application file for complete search history.

(56) References Cited

U.S. PATENT DOCUMENTS 5,861,406 A   1/1999   Wehrmann

OTHER PUBLICATIONS

Karmail et al., "Antitumor activity of CTO given orally in combination with temozolomide in the SC251 human glioblastoma model", Journal of Clinical Oncology, vol. 28, No. 15, Suppl., e13643. (May 20, 2010).*
Beers et al., The Merck Manual of Medical Information, Second Home Edition, p. 1045, (2003).*
Ge et al, Carboxyamido-triazole induces apoptosis . . . Clin Cacer Res 2000; 6: 1248-1254.
Ohn et al, In Vivo Efficacy of a Novel Inhibitor . . . Cancer Res 1992;52:32083212.
Allesandro et al, Effects of Carboxyamidotriazole . . . J.Cell Phys 2008; 215:111-121.
Corrado et al, Carboxyamidotriazole orotate . . . PloS One 2012;7:1-13.
Bauer et al, Carboxyamidotriazole . . . J Pharmacol Exp Therapeutics 2000;292:31-37.
Vogelstein et al, Cancer Genome Landscapes, Science Mag 2013, 339:1546-1558.
Mok et al, Gefitnib or carboplatin . . . , NEng J Med 2009, 361:947-957.
Martins et al, Cisplatin and . . . J Clin Oncology 2012; 46: 3299.
Yu et al, Analysis of Mechanisms . . . Clin Cancer Res , 2013; CCR-12-2246.
Chapman et al, Improved survival . . . NEJ Med 2011; 364:2507-2516.
Carrato et al, Fluorouracil, Leucovorin . . . , J Clin Oncol 2013; 31: 1341-1347.
Reck et al, Phase III of cisplatin plus . . . , J Clin Oncology 2009; 27: 2415.

* cited by examiner

*Primary Examiner* — Kevin E Weddington
(74) *Attorney, Agent, or Firm* — Rashida A Karmali

(57) ABSTRACT

This invention provides methods and compositions useful for treating early and late stage metastatic cancer to prevent or treat acquired resistance due to gene amplification or mutation in response to chemotherapeutic and/or targeted drugs. In particular, the methods and compositions include carboxiamidotriazole orotate (CTO) alone or in combination with specific regimens of chemotherapeutic and/or targeted drugs designed to overcome the genomic resistance raised to prior therapy.

19 Claims, 1 Drawing Sheet

Key Mutations in Ongonenic Signaling Pathways

NRAS: Q61L

KRAS: G12A, G12C, G12D, G12R, G12S, G12V, G13D

PI3K: E542K, E545K, H1047R

BRAF: BRAFC600E, BRAFV600K, BRAFV600R

EGFR: G719S, AE746-A750, L858R, L861Q, T790M, EGFRVIII,

ELREATS 746-752V

COMPOSITIONS FOR TREATING CANCERS HAVING ACQUIRED RESITANCE TO PRIOR CHEMOTHERAPEUTIC AND TARGETED DRUGS USING CARBOXYAMIDOTRIAZOLE OROTATE

CROSS-REFERENCE TO OTHER APPLICATION

This application is a Continuation-in-part of U.S. patent application Ser. No. 13/385,449 filed on Feb. 21, 2012, which is a Continuation-in-part of U.S. patent application Ser. No. 12/807,415 filed on Sep. 3, 2010, which issued as U.S. Pat. No. 8,377,973 on Feb. 19, 2013, which are incorporated herein, with references in their entirety.

1. FIELD OF INVENTION

This invention is related to a novel method for cancer therapy in patients with relapsed or refractory malignant cancers who have received prior therapy. More specifically, the invention is directed to overcoming the acquired resistance to traditional chemotherapeutic and targeted drugs caused by new mutations in oncogenes in the malignant cancers, by treating with carboxyamidotriazole orotate (CTO). This invention is based on unexpected and very important clinical effects of CTO observed in cancer patients having advanced or metastatic solid malignant cancers who volunteered to participate in Phase I clinical studies to study the safety of CTO. More specifically the invention relates to methods and compositions of CTO, to improve the progression free and overall survival and induce responses in some malignant cancers that were refractory to prior therapies thus overcoming resistance associated with new mutated oncogenes, heretofore, found to be untreatable. The invention is directed to overcoming the acquired resistance to prior therapy with traditional chemotherapeutic and targeted drugs which may be caused by mutations and amplification of genes and oncogenes and offering a rare therapy in later phases of cancer therapy. The invention is also directed in preventing the onset of acquired resistance to prior therapy with traditional chemotherapeutic and targeted drugs which may be caused by mutations and amplification of genes and oncogenes in later phases of cancer therapy. Currently, there is no option left for treatment of refractory cancers in the acquired resistance setting.

2. BACKGROUND TO THE INVENTION

Considerable progress has been made in the development of more effective regimens for the treatment of different types of solid cancers such as breast, colon, head and neck, malignant gliomas and glioblastoma, lung cancer, non-small cell lung cancer (NSCLC), melanoma, breast cancer, testicular cancer, carcinomas, sarcomas, lymphomas, pancreatic cancer, gastrointestinal stromal tumor, renal cancer, ovarian, prostate and others, and some leukemias such as chronic myeloid leukemia (CML).

Unfortunately, increased response rates to current chemotherapeutic and targeted therapy regimens have not been translated into marked improvements in survival since durations of response rates have been brief, and the natural history of the disease has ultimately remained unaltered. The development of drug resistance through amplification and development of new genes encoding protein kinases is a major obstacle to successful cancer therapy, given the important recent progress in treating different cancers through the use of multi-targeted kinase inhibitors. Great efforts have focused on the underlying mechanisms that turn promising targeted therapies which induce initial tumor shrinkage ineffective after a few months, resulting in refractory or untreatable cancers. Cytotoxic drugs are now used at some time during the course of the treatment of most cancer patients. Cytotoxic drugs can cure some primary and metastatic cancers and be effective in decreasing tumor volume, treating symptoms and even prolonging life in many types of cancers. However, survival rate has not been improved because these regimens are non-selective and related with systemic toxicities.

Therefore, molecular targeted therapy shows promise as an alternative treatment strategy since multiple molecular signaling pathways have been found to be dysregulated in most of the cancers such as breast, colon, head and neck, malignant gliomas and glioblastoma, lung cancer, NSCLC, melanoma, breast cancer, testicular cancer, carcinomas, sarcomas, lymphomas, renal cancer, pancreatic cancer, gastrointestinal stromal tumor, ovarian, prostate and others, and some leukemias such as chronic myeloid leukemia (CML).

Targeted therapy focuses on oncogenic signaling pathways specific to different cancers such as epidermal growth factor receptor (EGFR), human epidermal growth factor receptor 2 (HER-2), vascular endothelial growth factor receptor (VEGFR), insulin growth factor-1-receptor (IGF-1R), MET receptor, transcriptional factor nuclear factor kappa β (NF-kβ), KRAS, BRAF or phosphotidyl inositol-3-kinase (PI3K)/AKT/mammalian target of rapamycin (mTOR) pathway.

Targeted therapy focuses on any one of the oncogenic signaling pathways in patients with a cancer whose tumors harbor a specific mutation, and includes therapy with the inhibitor of the tyrosine kinase(s) involved with the expression of the mutation. Initial tumor shrinkage is generally observed but the cancer progresses because it acquires resistance to the specific or multi-targeted tyrosine kinase inhibitor (TKI) used by acquiring mutations in other oncogenes. Such gene amplifications represent a major reason for treatment failure because the specific or multi-targeted tyrosine kinase inhibitor is ineffective against the newly developed mutations. In addition, some of the TKIs currently in use and available may not be successful in silencing the specific mutation found in the cancer and thus not only will the mutation remain untreated but the TKI may induce amplification of new mutations.

The use of multi-targeted kinase inhibitors for cancer therapy is attractive because one agent can inhibit multiple kinases. Examples of multi-targeted kinase inhibitors include sunitnib (VEGFs, platelet-derived growth factor-PDGF), sorafenib, dasatinib, lapatinib, among others. However, these compounds are not effective after some cycles of treatment when gene amplification and new mutations induce acquired resistance to them.

The present invention also provides a method to modulate early and late changes induced by the chemotherapeutic and targeted drugs in inducing new oncogenes and gene amplifications to circumvent the TKI or chemotherapy and thus to prevent the resistance to antitumor activity to achieve treatment success. More particularly, CTO is selected because it has demonstrated the ability to inhibit multiple TKI pathways in multiple types of targets. Bauer et al 2000; Alessandro et al 2008; Corrado et al, 2012.

Importantly, and unexpectedly, CTO was found to inhibit amplification of the genes induced by a variety of prior therapies, including the multi-targeted kinases inhibitors currently in use, and to restore response in refractory cancers even when administered alone in advanced cancer patients. Thus, CTO has the potential to treat serious malignant cancers by demonstrating substantial improvement over existing therapies on stabilizing and or inducing responses in life threatening refractory cancers.

The present invention provides a method for i) evaluating the effect of adding CTO to chemotherapeutic and/or targeted drugs on the responsiveness of a specific tumor type, ii) identifying any new gene mutations and/or mechanisms that induce the resistance to the previously effective therapeutic drugs, iii) administration of CTO to treat refractory cancers, selecting cancers that respond to CTO and designing a regimen of CTO plus chemotherapeutic and/or targeted drugs to prevent of inhibit and resume responsiveness, and iv) determining the pharmacodynamic interaction between the prior cytotoxic and/or targeted drugs and CTO to achieve maximum efficacy, least drug resistance and successful treatment.

In other words, the present invention provides a method to prevent or treat new oncogene mutations and known targetable oncogenes with CTO to inhibit multiple tyrosine kinase (TKI) signaling pathways and unknown TKIs, in multiple types of tumor targets, as found unexpectedly in clinical studies of CTO in patients with different types of refractory malignant cancers having a wide spectrum of genomic mutations in the respective tumor tissues and having been given prior chemotherapeutic and multi-targeted drugs. This effect of CTO is distinguished from that of multi-targeted kinase inhibitors currently in use, in that CTO inhibits multiple TKI pathways currently being targeted with current multi-targeted TKIs as well as other TKIs that may have resulted due to mutations or gene amplifications when current TKIs are used. This novel use of CTO was found in refractory cancers that had acquired resistance to drugs through new mutations and gene amplification.

CTO is an orotate salt of Carboxyamidotriazole (CAI). CAI is an inhibitor of receptor-operated calcium channel-mediated calcium influx, and is shown to have antiproliferative and anti-invasive functions in several human cancer cell lines, including human glioblastoma cells (Ge et al, 2000). By interrupting calcium mobilization as a second messenger, CAI can inhibit calcium-sensitive signal transduction pathways, including the release of arachidonic acid and its metabolites; nitric oxide release; the generation of inositol phosphates; and tyrosine phosphorylation (Ge et al, 2000; Kohn et al, 1992). CAI inhibits VEGF expression and secretion (Bauer et al, 2000). CAI inhibits phosphorylation of cellular proteins STATS and CrkL, and induces apoptosis in imatinib mesylate-resistant chronic myeloid leukemia cells by down-regulating bcr-abl (Alessandro et al, 2008). CTO inhibits Akt and Erk1/2 phosphorylation in exosomes-stimulated HUVEC cell (Corrado et al, 2012), targets the tumors and mechanisms that may induce drug resistance or interfere with the antitumor activity.

The timing and duration of the CTO therapy may be determined to be from the start of the chemotherapy and/or targeted therapy or at various stages during the therapeutic regimen based on the understanding of the dynamics and extent of the effect of the chemotherapeutic and/or targeted drugs over expression and amplification of oncogenes or development of new mutations. Current principles guiding the selection of chemotherapeutic and/or targeted drugs do not consider their impact on oncogene amplification and new mutations that follow after a few courses of successful initial effective regimens. As a result it is only after the targeted cancers cease to respond and progress that other rescue drugs are tried, as a last resort. It is important to plan ahead and prevent the development of resistance in early stages, and also in later stages when cancers have become refractory to initial therapy with TKIs. However, the area of cellular signaling pathways of target kinases is poorly understood. This is why CTO, a multiple TKI in multiple tumor targets (and TKIs heretofore, not identified of understood but responsive to CTO) potentially provides a much needed method for cancer therapy in newly diagnosed and refractory cancers.

According to the method of the invention, it is 1) necessary to identify the genomic expression of a tumor, 2) to identify a profile of molecular targets in the tumor and select the appropriate targeted therapy and review from clinical literature and case studies whether to expect acquired resistance due to over expression of oncogenes or new mutations to potentially interfere with its anticancer activity, and 3) to select the most suitable combinatorial regimen of the cytotoxic drug, targeted therapy and CTO as part of an optimum therapeutic regimen. Among the problems currently associated with the use of cytotoxic and targeted drugs to treat cancers are the failure of targeted therapy after initial response, such failure resulting in progression of disease, and such failure likely caused by acquired resistance due to over expression of oncogenes and/or new mutations caused the therapy.

The combination of a cytotoxic drug with or without a targeted drug in addition to the multiple TKI, CTO thus provides more effective and sustained therapeutic paradigm for successful cancer treatment programs, a fundamental object of the invention.

3. SUMMARY OF THE INVENTION

The present invention seeks to meet an unmet need by using Carboxyamidotriazole Orotate (CTO) alone or in combination with traditional chemotherapeutic and/or targeted drugs in cancer therapy to achieve successful treatment outcomes and improved survival. The combinatorial therapy includes CTO to improve or maintain the sensitivity of the chemotherapeutic and targeted drugs to tumor cells, and to prevent or reduce the development of acquired resistance to either drug due to over expressing of oncogenes targeted and development of new mutations.

The invention provides methods and compositions for maintaining sensitivity of chemotherapeutic and targeted drugs by silencing the acquired resistance with timely combinatorial therapy with the multiple TKI CTO.

The invention provides a paradigm for the development of drug treatment regimens that are based on preclinical and clinical studies to provide molecular targeted therapy against multiple molecular signaling pathways found to be dysregulated in most of the cancers such as breast, colon, head and neck, malignant gliomas and glioblastoma, lung cancer, NSCLC melanoma, breast cancer, testicular cancer, carcinomas, sarcomas, lymphomas, pancreatic cancer, gastrointestinal stromal tumor, renal cancer, ovarian, prostate and others, and some leukemias such as chronic myeloid leukemia (CML), to achieve successful treatments and improve survival by preventing or treating the acquired resistance that is currently observed and that turns the cancers refractory.

The invention provides a paradigm that designs a suitable combinatorial regimen of the a targeted therapy and the multiple TKI, CTO to inhibit oncogenic signaling pathways specific to different cancers such as epidermal growth factor receptor (EGFR), human epidermal growth factor receptor 2 (HER-2), vascular endothelial growth factor receptor (VEGFR), insulin growth factor-1-receptor (IGF-1R), MET receptor, transcriptional factor nuclear factor kappa β (NF-kβ), KRAS, BRAF or phosphotidyl inositol-3-kinase (PI3K)/AKT/mammalian target of rapamycin (mTOR) pathway.

The invention provides a shift in the method of developing combinatorial drug regimens by requiring that varying doses of the chemotherapeutic and targeted drugs include CTO, to target acquired resistance due to over expression of oncogenes and/or development of new mutations. Currently, such combinations without CTO have resulted in many instances progression of cancer and poor survival.

The invention also provides pharmaceutical compositions comprising an effective amount of carboxyamidotriazole orotate to prevent or overcome acquired resistance to chemotherapeutic and targeted drugs due to gene amplification or mutation administered in the range 50 mg/m$^2$ to 1500 mg/m$^2$ based on the patient's body surface.

The invention further provides pharmaceutical compositions comprising an effective amount of carboxyamidotriazole orotate to prevent or overcome acquired resistance to chemotherapeutic and targeted drugs due to gene amplification or mutation administered in combination with one or more chemotherapeutic drugs and/or targeted drugs.

A further embodiment of the invention is development of a combinatorial regimen using just the targeted drug with CTO to prevent or overcome the acquired resistance to the targeted gene therapy to maintain the efficacy of the targeted drug against the tumor cells.

It is the object of the invention to provide methods to design optimum compositions of one or more chemotherapeutic and/or targeted drugs in combination with CTO to increase the effectiveness of the drugs selected, to improve the treatment effects and to reduce acquired resistance due to gene amplification and newly formed mutations. In other words, the invention provides a paradigm of achieving better efficacy, improving treatment effects over a prolonged period and improving the survival rates for different cancers.

Such an approach described above is based on unexpected important findings with when CTO was given to cancer patients with refractory cancers who volunteered to participate in Phase I clinical studies of CTO to establish its safety and tolerability. Importantly, it was found that some malignant cancers that were refractory to prior chemotherapeutic and/or targeted drugs showed clinical benefit to CTO by preventing progression of the disease and inducing partial responses. This novel and unexpected effect of CTO in overcoming acquired resistance to prior therapy is distinguished from CTO's effect in inhibiting tumor growth when given alone or in combination with chemotherapy in the early phase of the tumor growth before any other prior therapy is given. U.S. Pat. No. 5,861,406, issued Jan. 19, 1999. This invention provides an important, much needed and novel approach not only to obtain better efficacy using CTO in refractory cancers but also in early stages of therapy alone or in combination of chemotherapeutic and/or targeted drugs to achieve successful treatment and overall survival by inhibiting or preventing acquired drug resistance.

4. BRIEF DESCRIPTION OF FIGURES

FIG. 1 illustrates the key mutations of some of the oncogenic signaling pathways involved in different types of cancers and leukemia.

5. DETAILED DESCRIPTION OF THE INVENTION

The invention is achieved by evaluating molecular targets of chemotherapeutic and targeted drugs in different types of cancers and by exploiting some of the genomic changes linked to acquired resistance to the drugs by cancer cells. Protein kinases have proved to be important drug targets in oncology. The strategy of targeting the specific mutation has led to several targeted therapeutic agents, for example, trastuzumab (Herceptin) targeted to ERBB2/HER2; imatinib (Gleevec) targeted to BCR-ABL, KIT and PDFGR; gefitnib/erlotinib (Iressa/Tarceva) targeted to EGFR; vemurafenib targeted to BRAF V600, several PI3CA inhibitors in clinical trials, among others.

Despite development of molecular targeted therapy, the frequency of progression or recurrence of the disease after chemotherapeutic and/or targeted therapy has been unacceptably high. In case of chemotherapeutically pretreated recurrent tumors, it is challenging to determine an appropriate therapy for refractory cancers. In case of targeted therapy, it is important to overcome the acquired resistance by controlling the underlying mechanisms of gene amplification and or new mutations. This applies to a variety of different tumor types, for example, breast, colon, head and neck, malignant gliomas and glioblastoma, lung cancer, non-small cell lung cancer (NSCLC) melanoma, renal cancer, pancreatic cancer, gastrointestinal stromal tumor, ovarian, prostate and others, and some leukemia such as chronic myeloid leukemia (CML).

Chemotherapeutic drugs currently used in cancer therapy include, but are not limited to 5-Fluorouracil, 6-Mercaptopurine, Abraxane, Adriamycin, Affinitor, Alimta, Ara-C, BiCNU, Bleomycin, Capecitabine, Carboplatin, Carmoustine, CCNU, Cisplatin, Cyclophaosphamide, Dacarbazine, Daunomycin, Daunorubicin, Daunorubicin liposomal, Docetaxel, Doxorubicin, Doxorubicin liposomal, Epirubicin, Erbitux, Erbulin, Gemcitamide, Gliadel Wafer, Hydroxyurea, Irinotecan, Jakafi, Jevtana, L-asparaginase, Lenalidomide, Leucovorin, Liposomal ARA-C, Lomustine, Melphalan, Mercaptopurine, Methotrexate, Methotrexate sodium, Mitomycin, Nitrogen mustard, Oxaliplatin, Paclitaxel, paclitaxel protein bound, premetrexed, Rituxan, Sprycel, Taxol, Taxotere, Temodar, Temozolomide, Thalidomide, Topotecan, Tykerb, Velcade, Vinblastine, Vincristine.

Target drugs currently used or in clinical trial, include but are not limited to Alemtuzumab (Campath®), Alitretinoin (Panretin®), Anastrozole (Arimidex®), Bevacizumab (Avastin®), Bexarotene (Targretin®), Bortezomib (Velcade®), Bosutinib (Bosulif®), Brentuximab vedotin (Adcetris®), Cabozantinib (Cometriq™), Carfilzomib (Kyprolis™), Cetuximab (Erbitux®), Crizotinib (Xalkori®), Dasatinib (Sprycel®), Denileukin diftitox (Ontak®), Erlotinib hydrochloride (Tarceva®), Everolimus (Afinitor®), Exemestane (Aromasin®), Fulvestrant (Faslodex®), Gefitinib (Iressa®), Ibritumomab tiuxetan (Zevalin®), Imatinib mesylate (Gleevec®), Ipilimumab (Yervoy™), Lapatinib ditosylate (Tykerb®), Letrozole (Femara®), Nilotinib (Tasigna®), Ofatumumab (Arzerra®), Panitumumab (Vectibix®), Pazopanib hydrochloride (Votrient®), Pertuzumab (Perjeta™), Pralatrexate (Folotyn®), Regorafenib (Stivarga®), Rituximab (Rituxan®), Romidepsin (Istodax®), Sorafenib tosylate (Nexavar®), Sunitinib malate (Sutent®), Tamoxifen, Temsirolimus (Torisel®), Toremifene (Fareston®), Tositumomab and $^{131}$I-tositumomab (Bexxar®), Trastuzumab (Herceptin®), Tretinoin (Vesanoid®), Vandetanib (Caprelsa®), Vemurafenib (Zelboraf®), Vorinostat (Zolinza®); Ziv-aflibercept (Zaltrap®).

FIG. 1 lists some key mutations that have been found in some oncogenic signaling pathways in some of the different tumor types. In common solid tumors such as derived from the colon, breast, brain or pancreas, an average of 33 to 66 genes display subtle somatic mutations that would be expected to alter their gene products. Vogelstein et al, 2013. A few of these that responded to CTO, are discussed herein.

This invention contemplates treating these cancers and other cancers at any stage from the discovery of the cancer to the advanced stage, starting with the first step of carrying out the genotyping of the primary and secondary tumors. The effectiveness of the CTO treatment is determined by controlled clinical studies. The cancers are evaluated by measuring tumors no more than 14 days before the start of the treatment, and evaluated after 2 cycles of 28 days after day 1 of the administration of the first dose of CTO. The tumor size is measured by the most accurate measurement such as PET-CT, CT scan, MRI scan, x-ray, ultrasound, etc. The criteria for evaluating response are described in the revised Response Evaluation Criteria in Solid Tumors Guidelines, Eisenhauer et al, 1990 and by the Macdonald Criteria for response to high grade gliomas, Macdonald et al, 1990.

"Progressive disease" is defined as an increase of 25% or greater in the product of the largest perpendicular diameters for at least one bidimensionally measurable tumor, or an increase of 25% or greater at least one undimensionally measurable tumor or appearance of a new lesion or clinical deterioration.

"Stable disease" means a) for bidimensionally measurable tumors, less than a 50S decrease to less than a 25% increase in the sum of the products of the largest perpendicular diameters of all measurable tumors, b) for undimensionally measurable tumors, less than a 50% decrease to less than a 25% increase in the sum of the diameters of all tumors. For a) and b) no new tumors should appear.

"Partial response" means a) for bidimensionally measurable tumors, a decrease of at least 50% in the sum of the products of the largest perpendicular diameters of all measurable tumors as determined by two observations not less than four weeks apart, b) for undimensionally measurable tumors, a decrease by at least 50% in the sum of the largest diameters of all tumors as determined by two observation not less than four weeks apart. In cases where the patient has multiple tumors, it is not necessary for all tumors to have regressed to achieve a partial response as defined herein, but no tumor should have progressed and no new tumor should appear.

Head and Neck cancer is sixth most common type of cancer worldwide. Despite advances in treatment methods for head and neck cancer, the survival rate has not improved because treatment regimens are nonselective and toxic. Molecular target therapy is being developed since several oncogenic signaling pathways are involved such as EGFR, HER-2, VEGFR, IGFR, MET receptor, NF kB and PI3K/AKT. In head and neck cancer, targeting the epidermal growth factor EGFR has gained importance. Cetuximab, a chimeric mAb against EGFR improves the outcome of patients with recurrent metastatic disease. Martins et al 2013.

However, erlotinib, an oral tyrosine kinase inhibitor (TKI) of EGFR has showed no improvement when added to chemotherapy and radiotherapy. The mechanism of this lack of effect is unknown and it is unclear if acquired resistance is due to amplification of EGFR expression or due to new mutations.

In non-small cell lung cancer (NSCLC) treatment has improved by the identification of targeted therapies for a subset of molecularly defined lung cancers. Prospective studies of erlotinib and gefitnib in patients with EGFR mutant NSCLC has resulted in rates of success more than 60%. Mok T S, et al 2009. In addition, several new molecular targets in NSCLC have been identified, for example, HER2, BRAF and PI3K.

However, in NSCLC, various mechanisms of acquired resistance to erlotinib and gefitnib have been identified involving amplification of gene expression and new mutations. Understanding these mechanisms is critical to developing treatment strategies to maintain the response to erlotinib or gefitnib and prevent progression of the NSCLC. One mechanism of acquired resistance is the development of the new mutant EGFR T790M point mutation. Yu et al 2013. A new mutant would require a different TKI to inhibit this mutant, that is, a TKI different from that for erlotinib or gefitnib to overcome the acquired resistance.

PI3KCA mutations are also found lung adenocarcinomas and coexist with oncogenic mutation in EGFR or KRAS mutation. Multiple PI3K inhibitors are in development in clinical trials.

BRAF mutations have been identified in a variety of cancers including melanoma, colorectal cancer and papillary thyroid cancer. In melanoma the discovery of BRAF mutations has led to development of vemurafenib which has resulted in prolonged progression free and overall survival. Chapman et al 2011.

Panitumumab, a human IgG2 mAb, is currently approved for EGFR expressing metastatic colorectal cancer with disease progression on or following fluoropyrimidine oxaliplatin and irinotecan containing chemotherapy regimens. In colorectal cancer, the presence of BRAF mutations is associated with very poor prognosis.

Sunitnib, an oral multitargeted inhibitor of a vascular endothelial growth factors (VEGFs) and platelet-derived growth factor receptors (PDGF) and others, was tested in a FOLFIRI (fluorouracil, leucovorin, irinotecan) regimen, but did not prove superior over FOLFIRI alone. Carrato et al 2013. Sunitnib is used in the treatment of renal carcinoma, imatinib resistant gastrointestinal tumor, and pancreatic cancer.

Bevacizumab, a VEGF targeted mAB is shown to increase survival in patients receiving 5-Fluorouracil based chemotherapy for treatment of metastatic colorectal cancer, for treatment of NSCLS in combination with paclitaxel and carboplatin, for treatment of malignant gliomas and glioblastoma in combination with temozolomide, and for treatment of metastatic HER2 negative breast cancer in combination with paclitaxel. However, in most therapeutic regimens the response to bevacizumab is short lived and only small improvement is found because the tumor targets become refractory to treatment. With bevacizumab the acquired resistance is partly due to amplification of VEGF expression and/or increase in VEGF1 production. Reck et al 2009.

Example 1

In the present invention, when CTO, a multiple TKI was administered to a head and neck patient with refractory tumor previously treated with cetuximab, cisplatin and taxotere. The tumor's genomic mutations included PI3KCA, E545K. Treatment with cetuximab, an EGFR inhibitor had no clinical benefit. After having established the baseline clinical parameters, the patient was given 285 mg/m2/day for a period of 28 days for two cycles and the tumor was measured. It was found that the refractory tumor responded by not progressing. Stable disease and partial response were registered for more than six months. Progression free survival for six months is a good indicator of clinical effect. This suggests a potential use of CTO, a multiple TKI, in refractory head and neck cancer that had been treated with chemotherapeutic and targeted therapy. The treatment cycles and evaluations are continued until disease progression or unacceptable toxicity is encountered or patient withdraws voluntarily.

Example 2

In the present invention, a patient with NSCLC who had received prior treatment with paclitaxel, carboplatin erlotinib and docetaxel. The tumor had a mutation of PI3KCA, E545K. After having established the baseline clinical parameters, the patient was given 219 mg/m2/day for a period of 28 days for two cycles and the tumor was measured. It was found that the refractory tumor responded by not progressing. The treatment cycles and evaluations are continued until disease progression or unacceptable toxicity is encountered or patient withdraws voluntarily. Stable disease and partial response were registered for more than twelve months. Progression free survival for six months is a good indicator of clinical effect. This suggests a potential use of CTO, a multiple TKI, in refractory NSCLC that had been treated with an EGFR inhibitor and chemotherapeutic drugs but acquired resistance.

Example 3

Also, in the present invention, a patient with NSCLC who had received prior carboplatin, paclitaxel, docetaxel, erlotinib, cisplatin, gemcitamide and premetrexed and whose tumor remained refractory. The tumor mutations included EGFR, ELREATS 746-752 V (exon 19). After having established the baseline clinical parameters, the patient was given 219 mg/m2/day for a period of 28 days for two cycles and the tumor was measured. It was found that the refractory tumor responded by not progressing. The treatment cycles and evaluations are continued until disease progression or unacceptable toxicity is encountered or patient withdraws voluntarily. Stable disease and partial response were registered for more than twelve months. Progression free survival for six months is a good indicator of clinical effect. This suggests a potential use of CTO, a multiple TKI, in refractory NSCLC previously treated with chemotherapeutic and targeted therapy.

Example 4

In the present invention, it was unexpectedly found that a patient with metastatic colorectal cancer who had received prior therapy including leucovorin, fluorouracil, oxaliplatin, bevacizumab, cetuximab, capecitabine panitumumab and irinotecan, and whose tumor was refractory responded to CTO. The tumor had a mutation of BRAF V660E. After having established the baseline clinical parameters, the patient was given 285 mg/m2/day for a period of 28 days for two cycles and the tumor was measured. It was found that the refractory tumor responded to CTO by not progressing. The treatment cycles and evaluations are continued until disease progression or unacceptable toxicity is encountered or patient withdraws voluntarily. Stable disease and partial response were registered for six months. Progression free survival for six months is a good indicator of clinical effect. This suggests a potential use of CTO, a multiple TKI, in refractory colorectal cancer that had been treated with chemotherapeutic and targeted therapy. Three targeted drugs were used in prior treatment—bevacizumab, cetuximab and panitumumab—and even though it is not clear if one or more had induced acquired resistance; however, it is not clear that CTO overcame this and induced a response.

Example 5

In the present invention, it was unexpectedly found that a patient with renal cell carcinoma who had received prior therapy including IL-2, pegylated IFN, sorafenib, sunitnib, erlotinib and torisel, and whose tumor was refractory responded to CTO for over twelve months. After having established the baseline clinical parameters, the patient was given 75 mg/m2/day for a period of 28 days for two cycles and the tumor was measured. It was found that the refractory tumor responded by not progressing. The treatment cycles and evaluations are continued until disease progression or unacceptable toxicity is encountered or patient withdraws voluntarily. CTO was continued and stable disease and partial response were registered for more than twelve months. Progression free survival for six months is a good indicator of clinical effect. This suggests a potential use of CTO, a multiple TKI, in refractory colorectal cancer that had been treated with chemotherapeutic and targeted therapy.

The present invention is not to be limited in scope by the embodiment disclosed in the example which is intended as an illustration of one aspect of the invention and any methods which are functionally equivalent are within the scope of the invention. Indeed, various modifications of the invention in addition to those shown and described herein will become apparent to those skilled in the art from the foregoing description. Such modifications are intended to fall within the scope of the appended claims.

Those skilled in the art will recognize, or be able to ascertain using no more than routine experimentation, any equivalents to the specific embodiments of the invention described herein. Such equivalents are intended to be encompassed by the claims.

What is claimed is:

1. A pharmaceutical composition of an effective amount of carboxyamidotriazole orotate that prevents or overcomes acquired resistance to chemotherapeutic drugs and targeted drugs due to by gene amplification or mutation, wherein the effective amount of the composition is in the range 50 mg/m$^2$ to 1500 mg/m$^2$ based on the patient's body surface.

2. The pharmaceutical composition according to claim 1, further comprising one or more chemotherapeutic drugs of choice used in a regimen designed for overcoming acquired drug resistance and treating a cancer selected from the group consisting of breast, colon, head and neck, malignant glioma, glioblastoma, lung, non-small cell lung, melanoma, testicular, gastrointestinal stromal tumor, ovarian, prostate and chronic myeloid leukemia.

3. The pharmaceutical composition according to claim 1, further comprising one or more targeted drugs of choice used in a regimen designed for overcoming acquired drag resistance and treating a cancer selected from the group consisting of breast, colon, head and neck, malignant glioma, glioblastoma, lung, non-small cell lung, melanoma, testicular, gastrointestinal stromal tumor, ovarian, prostate and chronic myeloid leukemia.

4. The pharmaceutical composition according to claim 1, further comprising a chemotherapeutic drug of choice used in a regimen designed for treating a cancer and a targeted drug of choice used in a regimen designed for overcoming acquired drug resistance and treating a cancer selected from the group consisting of breast, colon, head and neck, malignant glioma, glioblastoma, lung, non-small cell lung, melanoma, testicular, gastrointestinal stromal tumor, ovarian, prostate and chronic myeloid leukemia.

5. The pharmaceutical composition according to claim 2 wherein the chemotherapeutic is paclitaxel.

6. The pharmaceutical composition of 3 wherein the targeted is erlotinib.

7. The pharmaceutical composition according to claim 2 wherein the chemotherapeutic drug is carboplatin.

8. The pharmaceutical composition according to claim 2 wherein the chemotherapeutic drug is premetrexed.

9. The pharmaceutical composition according to claim 2 wherein the chemotherapeutic drug is docetaxel.

10. The pharmaceutical composition according to claim 2 wherein the chemotherapeutic drug is lomustine.

11. The pharmaceutical composition according to claim 2 wherein the chemotherapeutic drug is gemcitabine.

12. The pharmaceutical composition of claim 3 wherein the targeted drug is cetuximab.

13. The pharmaceutical composition of claim 3 wherein the targeted drug is panitumumab.

14. The pharmaceutical composition of claim 3 wherein the targeted drug is imatinib.

15. The pharmaceutical composition of claim 3 wherein the targeted drug is trastuzumab.

16. The pharmaceutical composition of claim 3 wherein the targeted drug is bevacizumab.

17. The pharmaceutical composition of claim 3 wherein the targeted drug is vemurafenib.

18. The pharmaceutical composition of claim 3 wherein the targeted drug is ipilimumab.

19. The pharmaceutical composition of claim 3 wherein the targeted drug is tarceva.

\* \* \* \* \*